United States Patent [19]
Hengartner et al.

[11] 3,931,322
[45] Jan. 6, 1976

[54] SYNTHESIS OF 2-ALKYL-CYCLOPENTAN-1,3-DIONES

[75] Inventors: Urs Oskar Hengartner, Montclair; Pius Anton Wehrli, North Caldwell, both of N.J.

[73] Assignee: Hoffmann-La Roche Inc., Nutley, N.J.

[22] Filed: Jan. 25, 1974

[21] Appl. No.: 436,579

[52] U.S. Cl............................. 260/586 C; 260/483
[51] Int. Cl.². ....................................... C07C 45/00
[58] Field of Search ............................... 260/586 R

[56] References Cited
UNITED STATES PATENTS

| | | |
|---|---|---|
| 2,158,071 | 5/1939 | Hansley...................... 260/586 R X |
| 3,349,130 | 10/1967 | Bucourt et al. ................. 260/586 R |
| 3,504,036 | 3/1970 | Schick et al. .................... 260/586 R |
| 3,518,296 | 6/1970 | Bucourt et al. ............. 260/586 R X |
| 3,798,259 | 3/1974 | Wehrli ....................... 260/586 R X |

OTHER PUBLICATIONS

Crown Zellerbach, "Dimethyl Sulfoxide, Reaction Medium and Reactant," p. 1, (1962).

*Primary Examiner*—Norman Morgenstern
*Attorney, Agent, or Firm*—Samuel L. Welt; Jon S. Saxe; Raymond R. Wittekind

[57] ABSTRACT

2-Lower alkyl-cyclopentan-1,3-diones are prepared in high yield by cyclization of gamma-ketoesters in the presence of a colloidal suspension of an alkali metal primary lower alcoholate.

14 Claims, No Drawings

SYNTHESIS OF 2-ALKYL-CYCLOPENTAN-1,3-DIONES

BACKGROUND OF THE INVENTION

2-Lower alkyl-cyclopentan-1,3-diones are important intermediates for the total synthesis of steroids. A number of syntheses of this important class of intermediates have been reported, including syntheses which involve the cyclization of gamma-ketoesters in the presence of base. In particular, U.S. Pat. No. 3,349,130 to Bucourt, et al., teaches such cyclization in the presence of alkali metal tertiary alcoholates. French Pat. No. 1,564,830 to Watson, et al. teaches such cyclizations in the presence of sodium hydride.

Since alkali metal tertiary alcoholates and sodium hydride are relatively expensive and somewhat difficult to prepare in large quantities and are thus not practical for a large-scale commercial cyclization process, it would be desirable to have a cyclization method which would afford high yields of product and which would utilize relatively inexpensive and easy to prepare cyclization agents.

DETAILED DESCRIPTION OF THE INVENTION

The present invention involves the cyclization of gamma-ketoesters to afford 2-lower alkyl-cyclopentan-1,3-diones. In particular, the present invention relates to the preparation of lower alkyl cyclopentan-1,3-diones of the formula

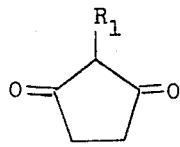  I wherein $R_1$ is lower alkyl by cyclization of gamma-ketoesters of the formula

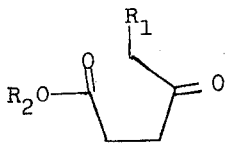  II wherein $R_1$ and $R_2$ are each lower alkyl. The term "lower alkyl" as used herein refers to a monovalent, saturated straight chain substituent consisting solely of carbon and hydrogen of up to 8 carbon atoms. Examples of lower alkyl groups are methyl, ethyl, n-propyl, n-butyl, n-hexyl, n-octyl, and so forth.

As can be seen from the above formulae, the cyclized products have a lower alkyl group ($R_1$) in the 2-position. Preferred products are 2-methyl-cyclopentan-1,3-dione and 2-ethyl-cyclopentan-1,3-dione.

The starting materials for the present invention are gamma-ketoesters, and the term "lower alkyl" for the substituent $R_2$ has the same significance as presented above for the substituent $R_1$. Examples of lower alkyl esters which may be utilized for the practice of the present invention are methyl esters, ethyl esters, n-propylesters, and so forth. Particularly preferred esters are methyl esters and ethyl esters.

In accordance with the present invention, the conversion of a gamma-ketoester of formula II to a 2-alkyl-cyclopentan-1,3-dione of formula I is carried out by heating the starting material in the presence of a colloidal suspension of an alkali metal primary lower alcoholate in an inert organic solvent medium.

Alkali metal primary lower alkyl alcoholates that may be utilized for the practice of the present invention include sodium alkyl alcoholates, potassium alkyl alcoholates and lithium alkyl alcoholates. Particular primary lower alky alcoholates which may be mentioned are methoxides, ethoxides, n-propoxides, and so forth. Preferred primary lower alkyl alcoholates are those derived from methanol and ethanol, that is, methoxides and ethoxides. Sodium methoxide and sodium ethoxide are particularly preferred and sodium methoxide is especially preferred.

It has been found that the unexpected results achieved by the present invention occur when utilizing a primary lower alkyl alcoholate as a colloidal suspension in an inert organic solvent medium. If the base is utilized in a different form, e.g., as a solid or a solution, inferior results are obtained.

Thus, for example, the addition of a commercially prepared (solid) sodium methoxide to a refluxing xylene solution of a gamma-ketoester affords significantly lower yields of cyclized material as compared with the use of a colloidal suspension of sodium methoxide, as described hereinafter.

A colloidal suspension of the alcoholate may be prepared by methods known per se for producing colloidal suspensions of materials of this type in organic media. A preferred method for preparing a colloidal suspension is by addition of a concentrated solution of the alcoholate in its corresponding alcohol (e.g., sodium methoxide in methanol) to refluxing or near refluxing solvent medium. In this manner, the lower boiling alcohol is readily distilled from the reaction mixture, usually as an azeotrope, leaving the alcoholate behind as a colloidal suspension.

As solvent media which may be mentioned for the practice of the present invention, there are hydrocarbons and substituted hydrocarbons. Examples of hydrocarbons are aliphatic hydrocarbons, e.g., heptane, octane, ligroine, etc. and benzene hdyrocarbons, e.g., benzene, toluene, xylene, etc. Examples of substituted hydrocarbons are chlorobenzene, bromobenzene, nitrobenzene and the like. A particularly preferred solvent for the present cyclization is xylene.

It has been found that especially favorable results may be obtained by the addition of small amounts of polar aprotic cosolvents to the reaction medium. Among the cosolvents which may be mentioned are dimethylformamide (DMF), dimethylsulfoxide (DMSO) and hexamethylphosphorictriamide (HMPT). A particularly preferred cosolvent is DMSO. The amount of cosolvent which may be added, to produce especially favorable results, is in the range of 0.1 to 2.0 equivalents relative to the gamma-ketoester being cyclized. An especially preferred range is from about 0.2 to about 0.5 equivalents.

The quantity of alkali metal primary alkyl alcoholate which may be utilized for the present cyclization may be in the range of from about 1 to about 5 equivalents relative to the gamma-ketoester being cyclized. An especially preferred range is from about 1 to about 2.5 equivalents.

The cyclization reaction is carried out at an elevated temperature in the range of from about 80° to about 250°C. It is preferred to carry out the cyclization at about the boiling point of the reaction medium. Thus, for a preferred solvent such as xylene, the reaction temperature would be in the range of from about 130° to about 140°C. The carrying out of the reaction at about the boiling point of the reaction medium affords several advantages, one of them being the formation The results in the following table were obtained by repeating the procedure of Example 1 on a 5 g scale, varying the quantity of base, the solvent and, in some cases, adding a cosolvent. The results indicate the effect of these variations. The overall lower yields, as compared with that in Example 1, are due to the smaller scale of the experiment. Yields comparable to that in Example 1 can be obtained by conducting the cyclization on a larger scale.

| Base | (equivalent) | Solvent | Cosolvent | (equivalent) | Yield |
|---|---|---|---|---|---|
| $NaOC_2H_5$ | 2 | xylene | | | 31% UV-assay[a] |
| $NaOCH_3$ | 2 | xylene | | | 48% recryst. |
| $NaOCH_3$ | 1 | xylene | | | 43% UV-assay[a] |
| $NaOCH_3$ | 1 | xylene | DMSO | 0.4 | 52% UV-assay[a] |
| $NaOCH_3$ | 1 | xylene | HMPT | 0.2 | 53% UV-assay[a] |
| $NaOCH_3$ | 1 | toluene | DMSO | 0.4 | 40% recryst. |
| $NaOCH_3$ | 1 | ligroine 90/120 | DMSO | 0.4 | 28% crude |

[a]UV-assay: crude yield × $\epsilon_{254}$ (crude)/$\epsilon_{254}$ (pure)

and distillation of an azeotrope of the hydrocarbon solvent with the alcohol of reaction, as well as that added for the introduction of the alcoholate, thus allowing for the removal of substantially all alcohol from the reaction mixture.

The process of the present invention is further illustrated by the following specific examples. It is to be understood that these examples are illustrative only of the invention and are not to be construed as limitative thereof in any manner.

EXAMPLE 1

Preparation of 2-methylcyclopentan-1,3-dione — Typical procedure

A 3 l. three-necked flask, equipped with a dropping funnel, a mechanical stirrer and a distillation head with thermometer and efficient Liebig condenser was charged with 1.4 l of xylene (b.p. 138°–141°). The xylene was stirred and heated to boiling, while 179 g of a 24% (wt/wt) sodium methoxide solution in methyl alcohol (43 g = 0.80 moles $NaOCH_3$) was added over 20 min. (the sodium methoxide solution was prepared by dissolving 23 g sodium in 203 g methyl alcohol). During this period, 450 ml of solvent was distilled off. After the addition was complete, 300 ml of xylene was added and the distillation was continued until the vapor temperature reached 138°. This resulted in the collection of an additional 250 ml of distillate. Then, 18 ml of dimethyl sulfoxide (Fisher) was added to the white suspension. A dropping funnel containing 100 g (0.633 moles) of 4-oxohexanoic acid ethyl ester in 200 ml of xylene was attached to the reaction flask; this solution was added to the vigorously stirred sodium methoxide suspension over 25 min. while 900 ml of solvent was distilled off continuously keeping the vapor temperature at 134°–137°. The orange-colored mixture was stirred and heated for further 5 min. and then allowed to cool to room temperature. Water was added, the mixture was acidified and the product was filtered, washed, dried and recrystallized from water to afford 50.6 g (71%) of 2-methyl-cyclopentan-1,3-dione, m.p. (uncorr.): 210°–211°C.

EXAMPLE 2

Preparation of 2-ethylcyclopentan-1,3-dione

A 1 l. three-necked flask, equipped with a dropping funnel, mechanical stirrer and a distillation head with thermometer and Liebig condenser was charged with 515 ml of xylene (b.p. 138°–140°), stirred and heated to boiling. 65.9 g of a 24% (wt/wt) sodium methoxide solution (prepared as in Example 1) in methyl alcohol (15.8 g = 0.293 moles) was added over 10 min., distilling off continuously the methyl alcohol. 300 ml of additional xylene were added and distillation was continued until the vapor temperature reached 135°. After the addition of 6.6 ml of dimethylsulfoxide, a solution of 40 g (0.232 moles) of 4-oxoheptanoic acid ethyl ester in 80 ml of xylene was added over 25 min. to the vigorously stirred sodium methoxide suspension while keeping the vapor temperature at ca. 135°C by continuous distillation of xylene. The orange-colored mixture was stirred and heated for an additional 5 min. and then allowed to cool to room temperature. Water was added, the mixture was acidified and the product filtered, washed, dried and recrystallized from water to afford 13.45 g (46%) of 2-ethyl-cyclopentan-1,3-dione, m.p. (uncorr.): 171°–172°C.

EXAMPLE 3

Preparation of 2-methylcyclopentan-1,3-dione using commercial sodium methoxide

A 250 ml three-necked flask, equipped with dropping funnel, mechanical stirrer and distilling head with condenser was charged with 3.4 g (63 mmoles) of sodium methoxide (Harshaw Chemical Co.) and 150 ml of xylene. The mixture was heated to boiling and a solution of 5 g (32 mmoles) of 4-oxohexanoic acid ethylester in 10 ml of xylene was added dropwise over a period of 10 min., while xylene was continuously distilled off keeping the vapor temperature at 135°. After the addition was complete, heating was continued for 1 hr. and the distilled solvent replaced from time to time by an equal amount of xylene. The reaction mixture was next cooled in an ice bath. Water was added and the mixture was acidified, the product filtered, washed and dried to afford 910 mg of slightly yellow crystals, m.p. 206°–210°. Crude yield: 25.7%; UV purity: 87%; corrected yield: 22.4%.

We claim:

1. A process for the preparation of a compound of the formula

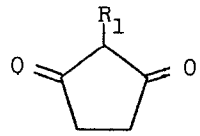

I wherein $R_1$ is lower alkyl, which comprises treating a compound of the formula

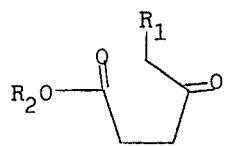

II wherein $R_1$ and $R_2$ are each lower alkyl, with a colloidal suspension of an alkali metal primary lower alkyl alcoholate in an inert organic solvent medium, at an elevated temperature.

2. The process of claim 1 wherein the alkali metal primary lower alcoholate is sodium methoxide.

3. The process of claim 1 wherein $R_1$ is methyl, that is, the compound of formula I is 2-methyl-cyclopentan-1,3-dione.

4. The process of claim 1 wherein $R_1$ is ethyl, that is, the compound of formula I is 2-ethyl-cyclopentan-1,3-dione.

5. The process of claim 1 wherein the inert organic solvent medium is selected from the group consisting of aliphatic hydrocarbons, benzene hydrocarbons and substituted benzene hydrocarbons.

6. The process of claim 5 wherein the solvent is xylene.

7. The process of claim 1 wherein the colloidal suspension of alkali metal primary lower alcoholate is prepared by addition of a concentrated solution of said alcoholate in its correspondong alcohol to the solvent medium at about reflux.

8. The process of claim 1 wherein the solvent medium contains between about 0.1 and 2.0 equivalents of a polar aprotic cosolvent, relative to the compound of formula II.

9. The process of claim 8 wherein between about 0.2 and 0.5 equivalents of cosolvent are utilized.

10. The process of claim 8 wherein the polar aprotic cosolvent is dimethylsulfoxide.

11. The process of claim 1 wherein between about 1 and 5.0 equivalents of alkali metal primary lower alcoholate are utilized.

12. The process of claim 11 wherein between about 1 and 2.5 equivalents of alkali metal primary lower alkyl alcoholate are utilized.

13. The process of claim 1 wherein the temperature is between about 80° and 250°C.

14. The process of claim 13 wherein the reaction temperature is at about the reflux point of the solvent medium.

* * * * *